US007070812B2

(12) United States Patent
Runge et al.

(10) Patent No.: US 7,070,812 B2
(45) Date of Patent: Jul. 4, 2006

(54) PROCESS FOR PRODUCING DRY POWDERS OF ONE OR MORE CAROTENOIDS

(75) Inventors: Frank Runge, Friedelsheim (DE); Erik Lüddecke, Mutterstadt (DE); Angelika-Maria Pfeiffer, Birkenheide (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/058,022

(22) Filed: Jan. 29, 2002

(65) Prior Publication Data

US 2002/0128325 A1    Sep. 12, 2002

(30) Foreign Application Priority Data

Jan. 31, 2001   (DE)  ................. 101 04 494

(51) Int. Cl.
*A61K 9/50*   (2006.01)
*A61K 9/14*   (2006.01)
*A61K 9/16*   (2006.01)

(52) U.S. Cl. ............. 424/499; 424/489; 424/490; 424/491; 424/493

(58) Field of Classification Search ............ 424/489, 424/490, 491, 493, 499
See application file for complete search history.

(56) References Cited

U.S. PATENT DOCUMENTS

| 3,110,598 | A |   | 11/1963 | Mueller et al. ............. 99/148 |
| 4,522,743 | A | * | 6/1985  | Horn et al. |
| 5,364,563 | A |   | 11/1994 | Cathrein et al. ............. 252/311 |
| 6,296,877 | B1 | * | 10/2001 | Auweter et al. |

FOREIGN PATENT DOCUMENTS

| CA | 2194796 | | 1/1996 |
| EP | 498 824 | | 8/1992 |
| EP | 0 937 412 | | 8/1999 |
| EP | 966 960 | | 12/1999 |
| GB | 887883 | | 1/1962 |
| WO | 91/06292 | * | 5/1991 |
| WO | WO 91/06292 | | 5/1991 |
| WO | WO 94/19411 | | 9/1994 |
| WO | 96/01570 | * | 1/1996 |

OTHER PUBLICATIONS

Jacobsen et al. "The pH-Stat and Its Use in Biochemistry" Methods of Biochemical Analysis vol. IV (1957) pp. 171-210.
Song et al. "On the Photoreceptor Pigment for Phototropism and Phototaxis is Cartenoid the Most Likely Candidate" Photochemistry and Photobiology, vol. 19 (1974) pp. 435-441.
Ruban et al. "Aggregation of higher plant xantophylls: differences in absorption spectra and in the dependency on solvent polarity" J. Photochem. and Photobiol. B: Biol. Fol. 21 (1993) pp. 229-234.
Salares et al. Excited State (Exciton) Interactions in Polyene Aggregates: J. of Raman Spectroscopy vol. 6 No. 6, (1977) pp. 282-288.
Manz et al. "Die Anwendung und Bedeutung von Synthetischen Carotinoiden in der Lebens-und Futternittel-sowie in der pharmazeutischen Industrie" Chimia vol. 21 (1967) pp. 329-335, Summary Considered only.

* cited by examiner

*Primary Examiner*—Humera N. Sheikh
(74) *Attorney, Agent, or Firm*—Novak Druce & Quigg, LLP; Jason D. Voight

(57) ABSTRACT

The invention relates to a process for producing dry powders of one or more carotenoids by a) dispersing one or more carotenoids in an aqueous molecular or colloidal solution of a mixture of lactose and a protective colloid and b) converting the dispersion which has formed into a dry powder by removing the water and, where appropriate, additionally used solvents and drying, where appropriate in the presence of a coating material, wherein at least one soybean protein is used as protective colloid in process step a).

21 Claims, No Drawings

PROCESS FOR PRODUCING DRY POWDERS OF ONE OR MORE CAROTENOIDS

The invention relates to a process for producing dry powders of one or more carotenoids, preferably of xanthophyll-containing dry powders, in particular of xanthophylls selected from the group consisting of astaxanthin, canthaxanthin, lutein, zeaxanthin, citranaxanthin and ethyl β-apo-8'-carotenoate.

The carotenoid class of substances is classified into two main groups, the carotenes and the xanthophylls. The carotenes, which are pure polyene hydrocarbons such as, for example, β-carotene or lycopene, differ from the xanthophylls which also have oxygen functionalities such as hydroxyl, epoxy and/or oxo groups. Typical representatives of the latter group are, inter alia, astaxanthin, canthaxanthin, lutein and zeaxanthin.

The oxygen-containing carotenoids also include citranaxanthin and ethyl β-apo-8'-carotenoate.

Oxygen-containing carotenoids are widespread in nature and occur inter alia in corn (zeaxanthin), in green beans (lutein), in paprika (capsanthin), in egg yolk (lutein) and in shrimps and salmon (astaxanthin), conferring on these foodstuffs their characteristic color.

These polyenes, which can both be obtained by synthesis and be isolated from natural sources, represent important coloring materials for the human food and animal feed industries and for the pharmaceutical sector and are, as in the case of astaxanthin, active substances with pro vitamin A activity in salmon.

Both carotenes and xanthophylls are insoluble in water, while the solubility in fats and oils is found to be only low, however. This limited solubility and the great sensitivity to oxidation stand in the way of direct use of the relatively coarse-particle products obtained from synthesis in the coloring of human foods and animal feeds because, in coarsely crystalline form, the substances provide only poor coloring results. These effects which are disadvantageous for use of xanthophylls in practice are particularly evident in an aqueous medium.

Improved color yields in the direct coloring of human foods can be achieved only by specifically produced formulations in which the active substances are in finely divided form and, where appropriate, protected from oxidation by protective colloids. In addition, use of these formulations in animal feeds leads to a greater bio availability of the carotenoids or xanthophylls and thus indirectly to improved coloring effects, for example in egg yolk or fish pigmentation.

Various processes have been described for improving the color yields and for increasing the absorbability or bio availability and all of them aim at reducing the size of the crystallites of the active substances and bringing the particles to a size in the region below 10 μm.

Numerous methods, inter alia described in Chimia 21, 329 (1967), WO 91/06292 and WO 94/19411, involve the grinding of carotenoids using a colloid mill and thus achieve particle sizes of from 2 to 10 μm.

There also exist a number of combined emulsification/spray drying processes as described, for example, in DE-A-12 11 911 or in EP-A-0 410 236.

According to European patent EP-B-0 065 193, carotenoid products in finely divided powder form are produced by dissolving a carotenoid in a volatile, water-miscible organic solvent at elevated temperatures, where appropriate under elevated pressure, and precipitating the carotenoid by mixing with an aqueous solution of a protective colloid and then spray drying.

An analogous process for producing carotenoid products in finely divided powder form is described in EP-A-0 937 412 with use of water-immiscible solvents.

The nanoparticulate dispersions of xanthophyll active substances produced as described in EP-B-0 065 193 frequently display the following phenomena, however.

The aqueous, xanthophyll-containing active substance dispersions are frequently colloidally unstable, especially on concentration. Flocculation of active substance particles, partly by sedimentation and partly by creaming, makes subsequent conversion of the dispersion into a dry powder impossible.

In addition, in the case of xanthophylls with carbonyl functionalities, there may be crosslinking of the gelatin employed as protective colloid to result in a gel which cannot be redispersed and which likewise cannot be converted into a dry powder.

Thus, the great demands on xanthophyll-containing formulations in relation to coloring effect and bio availability cannot always be met because of the problems described with the abovementioned process.

Another disadvantage of gelatins is that they have strongly adhesive properties. With the drying methods customary for liquid systems, such as spray drying or fluidized bed spray drying, on use of gelatin-containing products there may be thread formation or caking.

An additional factor is the diminishing acceptance of gelatin-containing products by consumers.

In other protective colloids which are often used, such as gum arabic, starch, dextrins, pectin or tragacanth, it is frequently possible to embed only relatively low concentrations of lipid-soluble substances. In addition gum arabic in particular has in the past not always been available in sufficient quality because of poor harvests.

Synthetic colloids such as polyvinylpyrrolidone or semi-synthetic polymers such as cellulose derivatives likewise show a limited emulsifying capacity and are not always accepted, especially in the human foods sector.

DE-A-44 24 085 describes the use of partially degraded soybean proteins as protective colloids for lipid-soluble active substances. The soybean proteins disclosed herein have a degree of hydrolysis of from 0.1 to 5%. The color strength of the formulations produced with these protective colloids is not always satisfactory.

It is an object of the present invention to propose processes for producing carotenoid-containing dry powders, in particular dry powders of oxygen-containing carotenoids, using protective colloids, which do not display the above-mentioned disadvantages of the prior art.

We have found that this object is achieved by a process for producing dry powders of one or more carotenoids by
 a) dispersing one or more carotenoids in an aqueous molecular or colloidal solution of a mixture of lactose and a protective colloid and
 b) converting the dispersion which has formed into a dry powder by removing the water and, where appropriate, additionally used solvents and drying, where appropriate in the presence of a coating material, wherein at least one soybean protein is used as protective colloid in process step a).

The protective colloids used according to the invention are one or more different soybean proteins. Preferred soybean proteins in this connection are those having a degree of hydrolysis ("DH") of from 0.1 to 20%, particularly preferably 3 to 12%, very particularly preferably 6 to 9%. The degree of hydrolysis "DH" is defined as follows:

$$DH = \frac{\text{Number of cleaved peptide bonds}}{\text{Total number of peptide bonds}} \times 100\%$$

The degree of hydrolysis can be determined by the so-called pH-stat method as described by C. F. Jacobsen et al. in "Methods of Biochemical Analysis", Vol. IV, pp. 171–210, Interscience Publishers Inc., New York 1957.

The partial degradation usually takes place enzymatically, suitable enzymes being proteases from plants, microorganisms, fungi, or animal proteases. The partial degradation is preferably carried out with the plant protease bromelain.

Soybean proteins usually employed are commercially available soybean protein isolates and concentrates with protein contents of from 70 to 90% by weight, the remaining 10 to 30% by weight representing other, more or less undefined, plant constituents. Soybean proteins which are preferably used in this connection are non-genetically modified soybean proteins.

The soybean protein isolates are incubated with the enzyme in an aqueous medium, preferably at temperatures of from 50 to 70° C. and pH values of from 7 to 9. The suitable ratio of protein to enzyme for the desired degree of hydrolysis in the individual case can be established in laboratory tests which are simple for the skilled worker.

The aqueous soybean protein hydrolyzate solutions are usually prepared so that the protein content is 6 to 10% by weight.

The weight-average molecular weight of the partially degraded soybean proteins used according to the invention is in the range from 15000 to 250000, preferably from 25000 to 220000, particularly preferably from 50000 to 200000, very particularly preferably in the range from 120000 to 180000.

It is also possible in the process of the invention to use mixtures of partially degraded soybean proteins with different degrees of hydrolysis or mixtures of partially degraded and undegraded soybean proteins as protective colloids. The weight-average molecular weights thereof in these mixtures are likewise in the abovementioned ranges.

The term dispersion preferably means the preparation of aqueous suspensions and of aqueous emulsions. The dispersion step a) particularly preferably comprises the preparation of a suspension of one or more carotenoids in an aqueous molecular or colloidal solution of a mixture of lactose and at least one soybean protein, in which the disperses phase comprises at least one of the active substances as nanoparticles.

A preferred embodiment of the abovementioned process comprises grinding the suspension prepared in process step a) before conversion into a dry powder. In this case, the active substance [the carotenoid(s)] is preferably suspended in crystalline form before the grinding process.

The grinding can take place in a manner known per se, for example using a ball mill. This entails, depending on the type of mill used, grinding until the particles have an average particle size D[4.3] determined by Fraunhofer diffraction of from 0.1 to 100 μm, preferably 0.2 to 50 μm, particularly preferably 0.2 to 20 μm, very particularly preferably 0.2 to 5 μm, especially 0.2 to 0.8 μm. The term D[4.3] refers to the volume-weighted average diameter (see Handbook for Malvern Mastersizer S, Malvern Instruments Ltd., UK).

Further details of the grinding and the apparatus employed therefor are to be found, inter alia, in Ullmann's Encyclopedia of Industrial Chemistry, Sixth Edition, 1999, Electronic Release, Size Reduction, Chapter 3.6.: Wet Grinding, and in EP-A-0 498 824.

A likewise preferred variant of the process of the invention comprises the dispersion in stage a) comprising the following steps:
- $a_1$) dissolving one or more carotenoids in a water-miscible organic solvent or in a mixture of water and a water-miscible organic solvent or
- $a_2$) dissolving one or more carotenoids in a water-immiscible organic solvent and
- $a_3$) mixing the solution obtained as in $a_1$) or $a_2$) with an aqueous molecular or colloidal solution of a mixture of lactose and at least one soybean protein, resulting in the hydrophobic phase of the carotenoid as nanodisperse phase.

Depending on the nature of the solvents used, the nanodisperse phase in step $a_3$) may comprise solid nanoparticles (suspension) or nanodroplets (emulsion).

The water-miscible solvents used in stage $a_1$) are, in particular, water-miscible, thermally stable, volatile solvents containing only carbon, hydrogen and oxygen, such as alcohols, ethers, esters, ketones and acetals. The solvents expediently used are those which are at least 10% water-miscible, have a boiling point below 200° C. and/or have fewer than 10 carbons. Those particularly preferably used are methanol, ethanol, n-propanol, isopropanol, 1,2-butanediol 1-methyl ether, 1,2-propanediol 1-n-propyl ether, tetrahydrofuran or acetone.

The term "a water-immiscible organic solvent" means for the purpose of the present invention an organic solvent with a solubility in water of less than 10% under atmospheric pressure. Possible solvents in this connection are, inter alia, halogenated aliphatic hydrocarbons such as, for example, methylene chloride, chloroform and tetrachloromethane, carboxylic esters such as dimethyl carbonate, diethyl carbonate, propylene carbonate, ethyl formate, methyl, ethyl or isopropyl acetate and ethers such as methyl tert-butyl ether. Preferred water-immiscible organic solvents are the following compounds from the group consisting of dimethyl carbonate, propylene carbonate, ethyl formate, ethyl acetate, isopropyl acetate and methyl tert-butyl ether.

The process of the invention preferably involves the production of dry powders of oxygen-containing carotenoids, particularly preferably compounds selected from the group consisting of astaxanthin, canthaxanthin, lutein, zeaxanthin, citranaxanthin and ethyl β-apo-8'-carotenoate.

The process of the invention is particularly preferably one wherein
a) astaxanthin and/or canthaxanthin is dissolved in a water-miscible organic solvent or a mixture of water and a water-miscible organic solvent at temperatures above 30° C.,
b) the resulting solution is mixed with an aqueous molecular or colloidal solution of a mixture of lactose and a partially degraded soybean protein with a degree of hydrolysis of from 0.1 to 20%, and
c) the dispersion which has formed is converted into a dry powder.

A process for producing astaxanthin-containing dry powders is very particularly preferred in this connection.

The abovementioned dry powders are advantageously produced in such a way that at least one of the carotenoids is dissolved in a water-miscible organic solvent at temperatures above 30° C., preferably between 50° C. and 240° C., in particular 100° C. to 200° C., particularly preferably 140° C. to 180° C., where appropriate under pressure.

Since exposure to high temperatures may in some circumstances reduce the desired high proportion of all-trans isomer, the dissolving of the carotenoid(s) takes place as quickly as possible, for example in the region of seconds, e.g. in 0.1 to 10 seconds, particularly preferably in less than 1 second. For rapid preparation of the molecular solution it may be advantageous to apply elevated pressure, e.g. in the range from 20 bar to 80 bar, preferably 30 to 60 bar.

To the molecular solution obtained in this way is subsequently added directly the aqueous molecular or colloidal solution, which is cooled where appropriate, of the mixture of lactose and soybean protein in such a way that a mixing temperature of about 35° C. to 80° C. is set up.

During this, the solvent component is transferred into the aqueous phase, and the hydrophobic phase of the carotenoid(s) results as nanodisperse phase.

Reference is made at this point to EP B-0 065 193 for a detailed description of the process and apparatus for the abovementioned dispersion.

The conversion into a dry powder can take place inter alia by spray drying, spray cooling, freeze drying or drying in a fluidized bed, where appropriate also in the presence of a coating material. Suitable coating agents are, inter alia, corn starch, silica or else tricalcium phosphate.

To increase the mechanical stability of the final product, it may be expedient in some cases to add a further plasticizer to the colloid, such as sugars or sugar alcohols, e.g. sucrose, glucose, glucose syrup, dextrin, invert sugar, sorbitol, mannitol or glycerol.

To increase the stability of the active substance to oxidative degradation it is advantageous to add stabilizers such as α-tocopherol, t-butylhydroxytoluene, t-butylhydroxyanisole, ascorbic acid or ethoxyquin. They can be added either to the aqueous or to the solvent phase, but they are preferably dissolved together with the active substances in the solvent phase.

It may also be advantageous in some circumstances additionally for a physiologically acceptable oil such as, for example, sesame oil, corn oil, cottonseed oil, soybean oil or peanut oil, and esters of medium chain-length vegetable fatty acids, in a concentration of from 0 to 500% by weight, preferably 10 to 300% by weight, particularly preferably 20 to 100% by weight, based on the xanthophyll(s), to be dissolved in the solvent phase and then precipitated as extremely fine particles together with the active substances and said additives on mixing with the aqueous phase.

The ratio of protective colloid and lactose to carotenoid is generally chosen so that the resulting final product contains between 0.1 and 30% by weight, preferably 1 to 25% by weight, particularly preferably 5 to 20% by weight, of carotenoid, 10 to 70% by weight of a protective colloid, and 10 to 70% by weight of lactose, all percentages based on the dry mass of the powder, and, where appropriate, small amounts of a stabilizer.

The invention also relates to dry powders of carotenoids obtainable by one of the processes mentioned at the outset.

These are preferably dry powders comprising oxygen-containing carotenoids selected from the group consisting of astaxanthin, canthaxanthin, lutein, zeaxanthin, citranaxanthin and ethyl β-apo-8'-carotenoate, particularly preferably canthaxanthin and astaxanthin, very particularly preferably astaxanthin.

The active substance content in the dry powders of the invention is in the range from 0.1 to 30% by weight, preferably 1 to 25% by weight, particularly preferably from 5 to 20% by weight, very particularly preferably in the range from 8 to 15% by weight.

The content of astaxanthin and/or canthaxanthin in the preparations of the invention is preferably in the range from 5 to 20% by weight.

The dry powders of the invention are distinguished inter alia by the fact that they can be redispersed without problems in aqueous systems to result in a uniform fine distribution of the active substance in the particle size range below 1 μm.

The use of a combination of lactose and soybean protein as formulation excipients has the advantage compared with sugars, for example glucose, that the carotenoid formulations produced therewith show a particularly good color strength together with improved bio availability.

Dry powders obtainable by the process of the invention have a higher apparent density than comparable formulations produced, for example, with glucose syrup. It has been found, surprisingly, that the higher apparent density simultaneously contributes to greater stability of the formulations of the invention.

It has additionally been found that colloidally stable and noncrosslinking nanoparticulate dispersions of oxygen-containing carotenoid active substances whose viscosity behavior approximately corresponds to that of Newtonian fluids are obtained. Fluids of this type are distinguished by their flow resistance, defined by Newton's equation $\tau = h \cdot D$, which is a material constant at a given temperature ($\tau$=shear stress, $D$=shear gradient, $h$=dynamic viscosity). Graphical representation of the flow behavior of Newtonian fluids gives approximately a straight line at a given temperature. In particular, the viscosity of the active substance dispersion changes by less than ±50% in the shear range between $10^{-2}$ sec.$^{-1}$ and $10^{+2}$ sec.$^{-1}$ at 40° C. and at 60° C.

The advantages of this approximately Newtonian viscosity behavior are, inter alia, that the active substance dispersions can be pumped more easily, especially after concentration, than is the case with pseudoplastic dispersions. In spray drying, in addition, the approximately Newtonian active substance dispersions have the advantage that the parameters of the spray head can be optimized more easily and that these dispersions behave less critically in the spray head.

On use of a mixture of partially degraded soybean proteins with a preferred degree of hydrolysis of >5% and lactose it is possible to produce xanthophyll-containing dry powders with the previously mentioned improved color strength and, in addition, an improved cold water redispersibility.

Partially degraded soybean proteins with a degree of hydrolysis of more than 5% surprisingly show better compatibility with the water-miscible solvents mentioned at the outset. This makes more concentrated procedures and thus a more economic process possible for producing the dry powders of the invention.

It has also been observed that the formation of H aggregates of xanthophylls is avoided in the process of the invention.

The aggregation of carotenoids is a phenomenon which has been disclosed in the literature and is described in numerous publications [P. Song, T. A. Moore, Photochemistry and Photobiology, 19, 435–441 (1974); A. V. Ruban, P. Horton, A. J. Young, J. Photochem. Photobiol. B: Biol., 21, 229–234 (1993); V. R. Salares, N. M. Young, P. R. Carey, H. J. Bernstein, Journal of Raman Spectroscopy, 6(6), 282–288 (1977)].

Carotenoid aggregates may, for example, be produced by mixing a solution of a carotenoid in a water-miscible organic solvent such as, for example, isopropanol, ethanol, acetone or tetrahydrofuran with water.

It is thus possible, as described in the abovementioned literature, to produce so-called H or J aggregates if the correct ratios of amounts of water and organic solvent are chosen.

H aggregates mean that the polyene chains are stacked like a pack of cards (card-stack aggregate), which can be characterized in the UV/vis spectrum by the appearance of a new band showing a hypsochromic shift compared with the absorption of the monomeric forms, in the range between 320 and 400 nm. J aggregates by contrast represent either a linear head-tail linkage (head-tail aggregates) of the polyenes, or they are arranged like fishbones (herringbone aggregates). Both arrangements cause a bathochromic shift in the UV absorption of the polyenes.

Feeding tests on trout have shown that H aggregates of xanthophylls, especially the H aggregates of astaxanthin, show a bio availability which is worse than that of the corresponding J aggregates, which represents a further advantage of the dry powders produced by the process of the invention.

The abovementioned dry powders are particularly suitable as addition to human foods and animal feeds and as addition to pharmaceutical preparations. Typical areas of use of the carotenoid-containing dry powders in the animal feeds sector are, for example, fish pigmentation in aquaculture and egg yolk and broiler skin pigmentation in poultry rearing.

The procedure for the process of the invention is explained in detail in the following examples.

EXAMPLE 1

Production of an Astaxanthin Dry Powder 48 g of crystalline astaxanthin, 1.6 g of ascorbyl palmitate and 20 g of a-tocopherol were suspended in 350 g of an azeotropic isopropanol/water mixture at room temperature in a heatable receiver. The active substance suspension was then heated to 90° C. and mixed at a flow rate of 2.1 kg/h continuously with further isopropanol/water azeotrope at a temperature of 223° C. with a flow rate of 2.7 kg/h, the astaxanthin dissolving at a mixing temperature of 165° C. which was set up, under a pressure of 55 bar. This active substance solution was immediately mixed with an aqueous phase consisting of a solution of 91 g of partially degraded soybean protein with a degree of hydrolysis of 7%, 182 g of lactose in 10540 g of distilled water, in which the pH was adjusted to 9.5 with 1 M NaOH, at a flow rate of 60 kg/h.

The active substance particles produced on mixing had a particle size of 132 nm in the isopropanol/water mixture, with an E1/1 value[1] of 127.

The active substance suspension was then concentrated in a thin film evaporator to a concentration of about 3.9% of active substance content and spray dried. The dry powder had an astaxanthin content of 12.8% by weight and an apparent density of 430 g/l. The dry powder redispersed in water had a particle size of 181 nm and an E1/1 value of 126.

[1] The E1/1 value defines in this connection the specific extinction of a 1% strength aqueous dispersion of a 10% by weight dry powder in a 1 cm cuvette at the absorption maximum.

COMPARATIVE EXAMPLE

Astaxanthin dry powder using a combination of soybean protein and glucose syrup 48 g of crystalline astaxanthin, 1.6 g of ascorbyl palmitate and 20 g of α-tocopherol were suspended in 350 g of an azeotropic isopropanol/water mixture at room temperature in a heatable receiver. The active substance suspension was then heated to 90° C. and mixed at a flow rate of 2.1 kg/h continuously with further isopropanol/water azeotrope at a temperature of 223° C. with a flow rate of 2.7 kg/h, the astaxanthin dissolving at a mixing temperature of 167° C. which was set up, under a pressure of 55 bar. This active substance solution was immediately mixed with an aqueous phase consisting of a solution of 91 g of partially degraded soybean protein with a degree of hydrolysis of 7%, 182 g of glucose syrup in 10540 g of distilled water, in which the pH was adjusted to 9.5 with 1 M NaOH, at a flow rate of 60 kg/h.

The active substance particles produced on mixing had a particle size of 146 nm in the isopropanol/water mixture, with an E1/1 value of 125.

The active substance suspension was then concentrated in a thin film evaporator to a concentration of about 3.6% of active substance content and spray dried. The dry powder had an astaxanthin content of 12.5% by weight and an apparent density of 400 g/l. The dry powder redispersed in water had a particle size of 347 nm and an E1/1 value of 101.

EXAMPLE 3

Canthaxanthin Dry Powder

Firstly 48 g of crystalline canthaxanthin, 4 g of ascorbyl palmitate and 16 g of α-tocopherol were suspended in 350 g of an azeotropic isopropanol/water mixture at room temperature. This active substance suspension was then heated to 88° C. and mixed continuously at a flow rate of 2.9 kg/h with further hot isopropanol/water azeotrope at a flow rate of 4.8 kg/h, the canthaxanthin dissolving at a mixing temperature of 175° C. which was set up, under a pressure of 55 bar. This active substance solution was then mixed with an aqueous phase consisting of a solution of 106 g of partially degraded soybean protein with a degree of hydrolysis of 7% and 219 g of lactose in 7050 g of distilled water, in which the pH had been adjusted to 9.5 with 1 M NaOH, at a flow rate of 52 kg/h.

The active substance particles produced on mixing had a particle size of 134 nm in the isopropanol/water mixture, with an E1/1 value of 133. This active substance dispersion was then concentrated in a thin film evaporator to a concentration of about 4.2% active substance content and spray dried. The dry powder had a canthaxanthin content of 12.4% by weight. The dry powder redispersed in water had an average particle size of 264 nm and an E1/1 value of 121.

We claim:
1. A method of improving the apparent density and stability of a dry powder of one or more carotenoids which comprises
   a) dispersing the one or more carotenoids in an aqueous molecular or colloidal solution of a mixture comprising effective amounts of lactose and a protective colloid, and optionally containing additional solvents, and b) converting the dispersion formed in step a) into a dry powder by removing the water and the additional solvents and drying, optionally in the presence of a coating material, wherein at least one soybean protein is used as protective colloid in process step a).

2. The method of claim 1, wherein the dispersing step a) comprises preparing a suspension of the one or more carotenoids in the aqueous molecular or colloidal solution of the mixture of lactose and the at least one soybean protein.

3. The method of claim 2, wherein the suspension prepared in step a) is ground before being converted into the dry powder in step b).

4. The method of claim 1, wherein the dispersing step a) comprises the following steps:
   $a_1$) dissolving the one or more carotenoids in a water-miscible organic solvent or in a mixture of water and a water-miscible organic solvent or
   $a_2$) dissolving the one or more carotenoids in a water-immiscible organic solvent and
   $a_3$) mixing the solution obtained in $a_1$) or $a_2$) with the aqueous molecular or colloidal solution of the mixture of lactose and the at least one soybean protein, to obtain a hydrophobic phase of the carotenoid in nanodispersed form.

5. The method of claim 1, wherein at least one partially degraded soybean protein with a degree of hydrolysis of from 0.1 to 20% is used as protective colloid.

6. The method of claim 1, wherein the carotenoids used are oxygen-containing carotenoids.

7. The method of claim 6, wherein the oxygen-containing carotenoids are compounds selected from the group consisting of astaxanthin, canthaxanthin, lutein, zeaxanthin, citranaxanthin and ethyl β-apo-8'-carotenoate.

8. The method of claim 7, wherein
   a) astaxanthin and/or canthaxanthin is dissolved in a water-miscible organic solvent or a mixture of water and a water-miscible organic solvent at temperatures above 30° C.,
   b) the resulting solution is mixed with an aqueous molecular or colloidal solution of a mixture of lactose and a partially degraded soybean protein with a degree of hydrolysis of from 0.1 to 20%, and
   c) the dispersion which has formed is converted into a dry powder.

9. The method of claim 8, wherein astaxanthin is used as carotenoid.

10. A carotenoid-containing dry powder having an improved apparent density and stability which is obtained by the method of claim 1.

11. A dry powder as claimed in claim 10 with a carotenoid content of from 0.1 to 30% by weight.

12. A dry powder as claimed in claim 10, comprising oxygen-containing carotenoids selected from the group consisting of astaxanthin, canthaxanthin, lutein, zeaxanthin, citranaxanthin and ethyl β-apo-8'-carotenoate.

13. A dry powder as claimed in claim 12, comprising 5 to 20% by weight of astaxanthin.

14. A dry powder as claimed in claim 12, comprising 5 to 20% by weight of canthaxanthin.

15. A human food, a pharmaceutical or an animal feed comprising the carotenoid-containing dry powder defined in claim 10 as an additive.

16. A carotenoid-containing dry powder having an improved apparent density and stability which is obtained by a process comprising
   a) dispersing one or more carotenoids in an aqueous molecular or colloidal solution of a mixture comprising effective amounts of lactose and a protective colloid, and optionally containing additional solvents, and
   b) converting the dispersion formed in step a) into a dry powder by removing the water and the additional solvents and drying, optionally in the presence of a coating material, wherein at least one partially degraded soybean protein having a degree of hydrolysis of from 0.1 to 20% is used as the protective colloid in process step a).

17. The dry powder defined in claim 16 wherein stage a) of the process comprises
   $a_1$) dissolving the one or more carotenoids in a water-miscible organic solvent or in a mixture of water and a water-miscible organic solvent, or
   $a_2$). dissolving the one or more carotenoids in a water-immiscible organic solvent, and
   $a_3$) mixing the solution obtained in $a_1$) or in $a_2$) with the aqueous molecular or colloidal solution of the mixture of lactose and the at least one soybean protein, to obtain a hydrophobic phase of the carotenoid in nanodispersed form.

18. The dry powder defined in claim 17 wherein stage a) of the process comprises
   $a_1$) dissolving the one or more carotenoids in a water-miscible organic solvent or in a mixture of water and a water-miscible, organic solvent at a temperature above 30° C., and
   $a_3$) mixing the solution obtained in $a_1$) with the aqueous molecular or colloidal solution of the mixture of lactose and the at least one soybean protein, to obtain a hydrophobic phase of the carotenoid in nanodispersed form.

19. The dry powder defined in claim 18 wherein the solution obtained in $a_1$) is mixed with the solution of the mixture of lactose and the soybean protein at a mixing temperature of from about 35° C. to 80° C.

20. A human food, a pharmaceutical or an animal feed comprising the dry powder defined in claim 16.

21. A method of improving the apparent density and color stability of a dry powder of one or more carotenoids which comprises
   a) dispersing the one or more carotenoids in an aqueous molecular or colloidal solution of a mixture comprising effective amounts of lactose and a protective colloid, and optionally containing additional solvents, and
   b) converting the dispersion formed in step a) into a dry powder by removing the water and the additional solvents and drying, optionally in the presence of a coating material, wherein at least one soybean protein is used as protective colloid in process step a).

* * * * *